United States Patent [19]

Gerharz

[11] Patent Number: 4,679,936
[45] Date of Patent: Jul. 14, 1987

[54] PROCESS AND APPARATUS FOR MEASURING OPTICAL DENSITY CHANGES AND TRANSIT TIMES IN TRANSPARENT MATERIALS

[75] Inventor: Reinhold Gerharz, Bethesda, Md.

[73] Assignee: The United States of America as represented by the Secretary of the Army, Washington, D.C.

[21] Appl. No.: 362,421

[22] Filed: Mar. 26, 1982

[51] Int. Cl.⁴ ............................................. G01N 21/41
[52] U.S. Cl. .................................................. 356/128
[58] Field of Search ........................... 356/5, 128, 73.1

[56] References Cited

U.S. PATENT DOCUMENTS 3,437,821 4/1969 Thompson et al. .................. 356/128
4,269,506 5/1981 Johnson et al. ......................... 356/5

Primary Examiner—R. A. Rosenberger
Attorney, Agent, or Firm—Max L. Harwell; Milton W. Lee; Anthony T. Lane

[57] ABSTRACT

A recirculating optical/electronic closed loop feedback process and apparatus in which nanosecond light pulses are triggered by a pulse generator upon arrival of previous signals that have just completed a round trip through the closed loop feedback system. The optical path is comprised of a light source and a detector between which is mounted beam forming optics that guide the light beam from the light source through a transparent vessel having a semitransparent medium therein whose refractive index and/or transparencies are measured. The electronic portion is comprised of a pulse amplifier for amplifying the detected light beam that in turn is repetitively applied to a high rate pulse generator to retrigger the light source through a pulse counter that records the number of signal circulations which pass through the closed loop during a given time to indicate the change of transmissivity of said medium.

12 Claims, 1 Drawing Figure

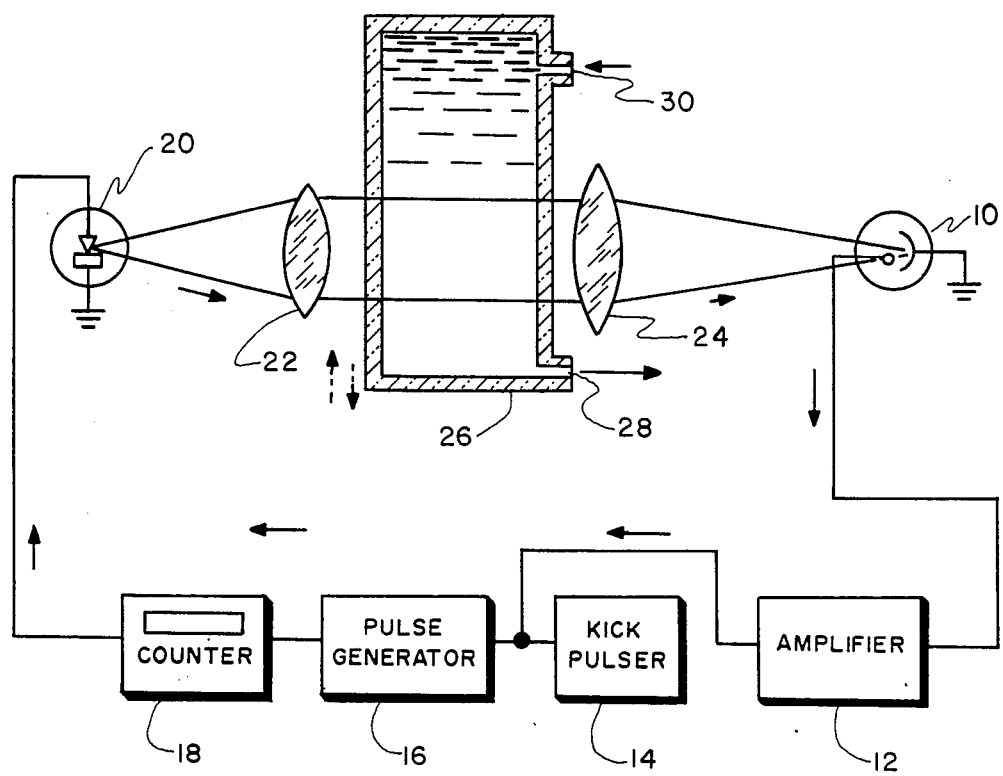

PROCESS AND APPARATUS FOR MEASURING OPTICAL DENSITY CHANGES AND TRANSIT TIMES IN TRANSPARENT MATERIALS

The invention described herein may be manufactured, used and licensed by the U.S. Government for governmental purposes without the payment of any royalties thereon.

BACKGROUND OF THE INVENTION

1. Field of the Invention

The invention is a recirculating optical/electronic closed loop process and apparatus in which nanosecond light pulses are repetitively passed through a light-transparent medium to test the time delay caused by a changing refractive index in the medium and to indicate any needed change in the constituency of the medium.

2. Description of the Prior Art

In process control technologies, there is a widespread need for a sensing data and apparatus which meaures and records optical density of materials or measures small distance variations between two or more reference points. The process control has application in fluid control devices or systems which, as examples, record the transmittance or the fluid level in vessels, determine the refractive index of such liquids, and replace displacement measuring devices that are predominantly used in the tool machine industry. In the past, level meters have ued complicated mechanical apparatus, refractometers have used optical devices with read-out techniques that depend on human obervers, and the displacement of materials was often recorded manually or semi-automatically by applying a measuring stick or tape or by some electrical read-out gadget. There is a need for obtaining minute changes in the detected data on the refractive index, over wide ranges of refractive index changes, represented as $n+\Delta n$, in light-transparent media. These refractive index changes may be used in controlling various process control operations.

SUMMARY OF THE INVENTION

The present invention employs the time domain of free traveling signals having a pulsed light source producing free traveling optical light pulses that pass through a transparent medium in an optical path and signal processing of the light pulses in an electronic portion of a closed loop feedback system.

The electronic portion is comprised of an externally triggered high rate pulse generator, possibly initially triggered by a lower pulse rate kick pulser, which produces very fast electronic signal pulses of short duration and at a large repetition rate. These electronic signal pulses pass through a pulse counter and repetitively trigger a light source. After each short duration light pulse from the light source travels through the optical path, a light detector cell receives electromagnetic radiation pulses, herein after referred to as optical light pulses but not necessarily limited to the optical range. The demodulated output from the detector cell is then amplified by a broadband amplifier with its output applied to the pulse generator. The pulse generator retriggers another pulse that proceeds through the pulse counter to the light source to again produce a short duration light pulse. The closed loop cycle is repeated with each nanosecond speed electronic and light pulse retriggering the subsequent pulse.

The refractive index of the transparent medium in the optical path determines the transient time of each pulse through the closed loop. In other words, the system uses the generation of optical transients for speed of light measurements in the transparent medium. The system utilizes the integration of minute signal delays during specific units of time. The transparent medium whose refractive index is being measured is preferably a liquid used in some process, such as checking for water in gasoline to checking more complex fluid mixtures, in which the constituents of the medium are being tested and measured. The signal propagation speeds in the transparent medium transmitting materials presupposes the knowledge of the refractive index $n_i$ and the wavelength $\lambda^1$ of the modulated probing optical signal.

The preferred embodiment of the present invention is the transmissive mode in the optical path with the pulsed light source and the light detecting means facing toward each other on opposite sides of the transparent medium. The system may operate in the reflective mode however wherein the pulsed light source and the light detecting means are on the same side of the medium and a reflective surface is on the opposite side of the medium.

Each element in the closed loop has a different refractive index, including the connections between elements in the electronic portion. Stated another way, the delay time in the closed loop is comprised of many delays representing each element and each connection with only the varying delay of the loop caused by the changing refractive index of the medium after the system has been previously settled down when the medium is not in the optical path. The delay time acts as the frequency which determines or indicates the refractive index of the transparent medium. The accuracy of the frequency measurement elements, such as the pulse counter and related elements, sets the limit of how well the refractive index and other factors are measured.

The speed measuring system in which the time required for a very short pulse, i.e. nanosecond pulse, to cycle through the closed loop varies according to the change in the refractive index of the transparent medium, which may be constantly flowing liquid, being tested in the continuous process, and the possible control system to maintain a set refractive index mixture of the liquid in the process. Circulation of each nanosecond pulse around the entire loop takes a certain amount of time. When operated repetitively wherein the initial pulse keeps retriggering subsequent pulses at the nanosecond frequencies, the pulse repetition rate that is established becomes a unique quantity inversely proportional to the delay caused by the refractive index of the liquid medium being monitored and controlled. The number of pulses recorded on the pulse counter in a precisely timed period of time converts to the refractive index changes in the continuously flowing light transparent medium being monitored. The system allows continuous monitoring of the liquid medium without disturbing the medium itself. The light pulse beam penetrates the medium after passing through beam forming optics. The light pulse beam may be focused in a small portion of the medium to measure the refractive index only in localized areas or defocused over a much larger area. If the frequency is measured by counting pulses for 1 second and the count is accurate to 1 pulse, the frequency is within an accuracy of 1 part in $10^6$. The present frequency measurement apparatus is within that accuracy.

The invention will be described with further detail in reference to the lone FIGURE.

BRIEF DESCRIPTION OF THE DRAWING

The lone FIGURE is a schematic illustration of the process control apparatus and system of the present invention.

DETAILED DESCRIPTION OF THE PREFERRED EMBODIMENT

Referring now to the FIGURE, transmit times of the electromagnetic, i.e. optical signals, are used for sensing the refractive index and/or transparency measurements. Arrows are used to indicate the direction of signal flow. A separate kick pulser generator 14 may be used to trigger an electric pulse signal from pulse generator 16 through a pulse counter 18 to a pulsed light source 20. Pulsed light source 20 amplifies and converts the electric pulse signal to a free-traveling pulse of optical radiation. The light source 20 may be a light emitting diode (LED). Many LED components are available that emit light of various colors, some of which emit non-visible light or mircowave radiation, such as Gunn-oscillators.

An electric pulse signal generated from pulse generator 16 of about 2 volts driving amplitude was found sufficient to modulate a LED with a 5 nanosecond light pulse, at a wavelength $\lambda$ of 650 nanometer, at a starting pulse repetition frequency of about 15 MHz, but may be up to 20 MHz. Optical elements 22 and 24 of beam forming optics direct the optical radiation pulse through a vessel 26 which has transparent walls through which the radiation passes and which contains the transparent medium, which may be a liquid, that is being tested. The liquid may enter tube 30 and exit tube 28. The vessel 26 itself may be moved in and out of the optical path of elements 22 and 24, say by a slide carriage system. The light source 20 is preferably positioned into the focus of lens 22. The optical radiation signal is passed through the vessel 26 walls and the transparent liquid and is focused into a radiation detecting means 10, such as a light detector cell. The detector cell may be a photoelectron multiplier (PM) since the PM would readily provide the necessary amplification capable of measuring a difference intensity of the light pulse. The detector cell may also be a phototransistor or a photocell.

Upon arrival of each optical radiation pulse at the detector cell 10, a new electric pulse signal is created which enters a wideband amplifier 12 that amplifies the new electric pulse signal which is applied to the pulse generator 16. Another electric pulse signal is then emitted from generator 16 which will transit the closed loop as previous pulses have. The signal circulation rate, i.e. the signal repetition frequency $F_r$, is automatically repeated. The repetition frequency $F_r$ depends only on the electrical/optical signal transit time of all components in the signal propagation loop. All electronic elements are preferably connected together with low loss coaxial cable. The transparent medium, which is being tested, is made a part of this loop and effects the Fr by its length and characteristic transit time, while all the other transit times of elements in the loop can be arranged to remain constant. In this manner, when a change in the refractive index of the liquid medium occurs by change in the amount of constituent materials in the liquid a different signal transit time also occurs which causes a varying signal circulation rate in the closed loop.

The refractive index n is defined as the ratio of two group velocities of electromagnetic signals, $n_i = c_o/c_i$, where $c_o = 3 \times 10^{10}$ cm/sec, i.e. the speed of light in vacuum. The equivalent refractive index for the entire loop is therefore: $n_i = c_o/c_i = c_o/(s \cdot F_r)$, if s is the totaled electromagnetic length of the propagation loop. Alternatively, statements of signal propagation speeds in transmitting materials presuppose the knowledge of the refractive index $n_i$ and the wavelength $\lambda$ of the modulated probing signal. It is obvious that each element i of the loop may have a different refractive index, which then may be determined from its individual signal transit time $n_i = c_i \cdot t_i / \Delta s_i$, i.e. from frequency difference measurements $\Delta f = F_r \pm f$, at the various length settings $\Delta s$ of the loop.

Once the process control system has been started, the automatic recirculation of the signals will be repetitive in the same mode, with all round trips over the closed loop counted by the pulse counter 18 and registered as the signal repetition frequency $F_r$. The pulse counter 18 may be tuned circuits or electronic counters. The quantity $F_r$ reflects the integrated number of signal transits through the loop per unit of time, $F_r = (1/T_{loop})$. Obviously, the time for one loop transit $T_{loop}$ is identical to the sum total of all transit times through the individual elements. Tests have confirmed very uniform triggering action of the pulse generator 16 even for large changes of transit time, which is introduced by the insertion of various time delay elements into the loop.

The signal speed $c_n$ through the vessel 26 and the transparent medium therein can be determined from the measurement of two signal repetition frequencies, one measured when the vessel 26 is empty and one measured when the transparent medium being meaured or tested is present in the vessel, by using the equation, $$c_n = \Delta s (1/f - f/F)^{-1}, \qquad (1)$$

where, F is the original frequency of signal repetition when the vessel is empty, f is the new frequency of the vessel and the transparent medium therein combined, and $\Delta s$ is optical path length of the empty vessel, the signal speed can be determined. Many transparent mediums have a well defined transit time that is known to be better than one part in $10^6$, if the wavelength of the transiting signal is known. If such quantity is known, and herein indicated as $c_i$, while the signal transit time through vessel 26 when empty is indicated as $c_o$, the ratio of the two transit times equals the refractive index n of the medium: $n = c_o/c_n$. There is dispersion caused by constituents in the transparent medium. The derivative, represented as D, of the refractive index in respect to the wavelength of the transiting signal is identical with the transparent medium's dispersion: $D = dn/d\lambda$. Measurements as to incremental changes of distance, represented by $\Delta s$, across the optical path between the pulse light source 20 and the pulse detecting means 10 are as follows:

$$\Delta s = \pm c(1/f - 1/F) \qquad (2)$$

where c is the signal transit time through the closed loop and f and F are as defined with reference to Equation (1). The invention provides rapid access to the above data without disturbing the medium and facilitates other applications of process control means to the handling, treatment, or manufacturing of the medium with a minimum of delays. Even though the short duration pulses are explained herein as in nanoseconds and for example about 2 volts driving amplitude, the pulses may be in the millisecond to nanosecond range and in the 2 to 200 volt amplitude range.

I claim:

1. An apparatus for measuring the speed of light changes through a transparent medium whose refractive index and transparency are changing in a continuous process, said apparatus comprised of:

a closed loop feedback system comprised of an optical link and an electronic portion wherein free traveling pulses of optical radiation are guided in said optical link from a light source through a transparent vessel containing said transparent medium and onto a radiation detecting means by beam forming optics wherein said radiation detecting means demodulates each of said pulses of optical radiation that is converted into electrical pulses in said electronic portion wherein said electrical pulses from said radiation detecting means is applied to a wideband amplifier which triggers an externally triggered high rate pulse generator into producing short duration electrical pulses therefrom through a pulse counter to drive said light source into propagating said free traveling pulses of optical radiation through said optical link wherein the mutually complementary optical and electrical pulses are automatically repeated through said closed loop feedback system in which the pulse repetition rate as recorded by said pulse counter establishes new freely circulating frequencies which are inversely proportional to the transit delay of said pulses of optical radiation caused by the changing optical density of the constituents in said transparent medium that are being measured in said continuous process.

2. The apparatus as set forth in claim 1 wherein said light source is a light emitting diode.

3. The apparatus as set forth in claim 2 wherein said radiation detecting means is a photoelectron multiplier.

4. The apparatus as set forth in claim 3 wherein said electrical pulses and said pulses of optical radiation are from the millisecond to the nanosecond range.

5. The apparatus as set forth in claim 3 wherein said short duration electrical pulses produced from said pulse generator are in the 2 to 2000 volts range of driving amplitude with a 5 nanosecond pulse at a wavelength of 650 nanometers at a starting pulse repetition rate of about 15 mega-Hertz.

6. The apparatus as set forth in claim 5 wherein said light source and said radiation detecting means are positioned in the focal region of said beam forming optics.

7. The apparatus as set forth in claim 6 wherein said optical link operates in the transmissive mode wherein said light source and said radiation detecting means face each other on opposie sides of said transparent medium with said pulses of optical radiation transmitted therethrough.

8. The apparatus as set forth in claim 6 wherein said optical link operates in the reflective mode wherein said light source and said radiation detecting means are on the same side of said transparent medium with a reflective surface on the opposite side of said transparent medium to back reflect said pulses of optical radiation therefrom.

9. The apparatus as set forth in claim 1 wherein said externally triggered high rate pulse generator is initially triggered by a kick pulser.

10. The apparatus as set forth in claim 5 wherein said pulse counter has a preset counting period of discrete time intervals.

11. A process of measuring the changing refractive index in a flowing transparent liquid medium on a continuous basis comprising the steps of:

circulating said transparent liquid medium through an enclosed transparent vessel;

transmitting pulses of optical radiation through said vessel and transparent liquid medium;

detecting said pulses of optical radiation;

demodulating and converting the detected pulses of optical radiation into electrical pulses;

amplifying said electrical pulses and applying to an externally triggered high rate pulse generator for producing short duration electrical pulses therefrom;

counting said short duration electrical pulses over a preset counting period; and driving a light source in accordance with the arrival of said short duration electrical pulses to propogate the transmitted pulses of optical radiation wherein the process is automatically repeated with the step of said externally triggered pulse generator producing short duration electrical pulses for each repetitive cycle of the mutually complementary optical and electrical pulse in which the pulse repetition rate establishes frequencies which are inversely proportional to transit time delays through said transparent liquid medium.

12. A process as set forth in claim 11 wherein the step of transmitting pulses of optical radiation is comprised of optically forming said optical radiation into desired focused beams of optical radiation at said transparent liquid medium.

* * * * *